US012065461B2

(12) United States Patent
Sarac et al.

(10) Patent No.: US 12,065,461 B2
(45) Date of Patent: Aug. 20, 2024

(54) METHOD FOR PREPARING 3'-O-AMINO-2'-DEOXYRIBONUCLEOSIDE-5'-TRIPHOSPHATE

(71) Applicants: DNA Script, Le Kremlin-Bicêtre (FR); Institut Pasteur, Paris (FR); Centre National de la Recherche Scientifique, Paris (FR)

(72) Inventors: Ivo Sarac, Paris (FR); Marcel Hollenstein, Paris (FR)

(73) Assignees: DNA Script, Le Kremlin-Bicêtre (FR); Institut Pasteur, Paris (FR); Centre National de la Recherche Scientifique, Paris (FR)

( * ) Notice: Subject to any disclaimer, the term of this patent is extended or adjusted under 35 U.S.C. 154(b) by 721 days.

(21) Appl. No.: 17/270,409

(22) PCT Filed: Aug. 29, 2019

(86) PCT No.: PCT/EP2019/073135
§ 371 (c)(1),
(2) Date: Feb. 22, 2021

(87) PCT Pub. No.: WO2020/043846
PCT Pub. Date: Mar. 5, 2020

(65) Prior Publication Data
US 2021/0214382 A1  Jul. 15, 2021

(30) Foreign Application Priority Data

Aug. 31, 2018 (EP) .................................... 18306151

(51) Int. Cl.
*C07H 1/04* (2006.01)
*C07H 21/04* (2006.01)

(52) U.S. Cl.
CPC .............. *C07H 1/04* (2013.01); *C07H 21/04* (2013.01)

(58) Field of Classification Search
None
See application file for complete search history.

(56) References Cited

U.S. PATENT DOCUMENTS

| 6,274,383 | B1 | 8/2001 | Gao |
| 7,544,794 | B1 | 6/2009 | Benner |
| 8,034,923 | B1 * | 10/2011 | Benner .................. C07H 19/20 536/25.31 |
| 8,212,020 | B2 | 7/2012 | Benner et al. |

FOREIGN PATENT DOCUMENTS

WO  2010110775  9/2010

OTHER PUBLICATIONS

Maillard et al. J. Org. Chem. (2005), vol. 70, pp. 6303-6312.*
Hutter et al. (2010) "Labeled Nucleoside Triphosphates with Reversibly Terminating Aminoalkoxyl Groups" Nucleosides, Nucleotides & Nucleic Acids, 29 (11-12): 879-895.
Swamy, K.C.K. et al (2009). "Mitsunobu and Related Reactions: Advances and Applications," Chem. Rev. 109: 2551-2651.

* cited by examiner

*Primary Examiner* — Patrick T Lewis
(74) *Attorney, Agent, or Firm* — Morrison & Foerster LLP

(57) ABSTRACT

The invention relates to a method for preparing 3'-O-amino-2'-deoxyribonucleoside-5'-triphosphate. It also relates to a solid support functionalized with at least one N-hydroxyphthalimide moiety and uses thereof for protecting 3'-hydroxy group of a 2'-deoxyribonucleoside during synthesis of a nucleoside or a derivative thereof.

13 Claims, 1 Drawing Sheet

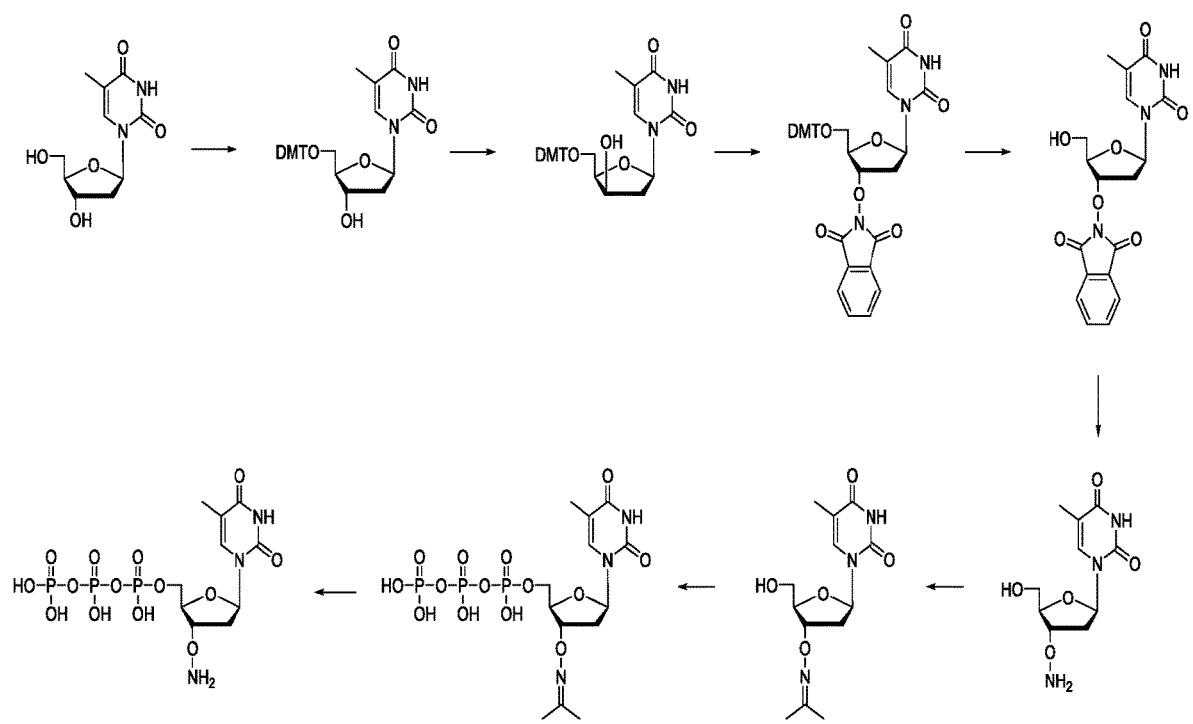

METHOD FOR PREPARING 3'-O-AMINO-2'-DEOXYRIBONUCLEOSIDE-5'-TRIPHOSPHATE

TECHNICAL FIELD

The invention relates to a method for preparing 3'-O-amino-2'-deoxyribonucleoside-5'-triphosphate. It also relates to a solid support functionalized with at least one N-hydroxyphthalimide moiety and uses thereof for protecting 3'-hydroxy group of a 2'-deoxyribonucleoside during synthesis of a nucleoside or a derivative thereof.

TECHNICAL BACKGROUND

Besides their role in the storage, expression and transmission of genetic information, nucleic acids are known for their therapeutic potential. The first strategy, which aimed at treating monogenic diseases by supplementing a defective gene with a "healthy" gene, was extended over the last years, to new therapeutic strategies for treating various diseases, in particular cancers. Breakthroughs in this field are strongly supported by the development of chemical or enzymatic methods for synthetizing nucleic acids. The chemical synthesis of nucleic acids has been the subject of intensive researches since 1950, and has led to more and more efficient strategies. The original use of phosphotriester and H-phosphonate moieties for coupling 3'-hydroxy group of a nucleoside with 5'-hydroxy group of another nucleoside, was later replaced by a phosphoramidite moiety, which is still widely used nowadays. A further improvement was brought by the development of solid support synthesis of nucleic acids, which simplifies the separation of products in the reaction mixture. The enzymatic approach covers a set of techniques, such as polymerase chain reaction (PCR) and rolling circle amplification (RCA), which use a polymerase, a primer, and nucleoside triphosphates. This approach allows to obtain very long chains in a short time, and also to use modified nucleoside triphosphates, provided that said modifications are tolerated by the polymerase. In particular, nucleoside triphosphates are generally subjected to the blocking of their 3'-hydroxy with a removable protecting group or "blocking group". Recently, 3'-O-aminated nucleoside derivatives have sparked scientists' attention due to the great potential of the amino group as blocking group. The amino group is stable and small, which makes it most likely to be accepted by the polymerase. However, one major difficulty lies in the preparation of such a compound, which implies the control of reactions' selectivity relative to 3'- and 5'-hydroxy groups but also the amino group.

U.S. Pat. Nos. 7,544,794 and 8,212,020 describe the synthesis of a 3'-O-amino-2'-deoxyribonucleoside-5'-triphosphate starting from the corresponding 2'-deoxyribonucleoside. After protection of the 5'-hydroxy group, a O-amino moiety is brought in a "masked" (or "protected") form by a N-hydroxyphthalimide moiety, which is inserted at the 3' position, through two subsequent hydroxy inversions under Mitsunobu conditions. Both 3'-O-amino group and 5'-hydroxy group of the nucleoside are then deprotected. However, the triphosphorylation of the 5'-hydroxy group requires that the 3'-O-amino group be protected again. The 3'-O-amino group is protected in the form of an oxime and is finally deprotected after the triphosphorylation reaction (see FIG. 1). This synthesis is carried out in solution, and thus requires further purification steps. In particular, the presence of a phosphine, converted into phosphine oxide, in Mitsunobu reactions makes said purifications more difficult.

Thus, there remains a need to provide a simple and efficient method for preparing 3'-O-amino-2'-deoxyribonucleoside-5'-triphosphate, with a reduced number of steps and simplified purification steps.

SUMMARY OF THE INVENTION

In this respect, the inventors have demonstrated that the use of a solid support functionalized with at least one N-hydroxyphthalimide moiety in the synthesis of 3'-O-amino-2'-deoxyribonucleoside-5'-triphosphate allows to reduce the number of steps, in particular protection/deprotection steps. It has further been shown that the use of such a solid support, which remains in suspension and not in solution, simplifies purification steps, even for Mitsunobu reactions. In the method of the invention, the O-amino moiety is brought in a "masked" (or "protected") form through insertion of the N-hydroxyphthalimide moiety linked to the solid support, and is kept in such a form all along the synthesis. The 3'-O-amino group can be deprotected in a final cleaving step.

Thus, the present invention relates to a method for preparing 3'-O-amino-2'-deoxyribonucleoside-5'-triphosphate, said method comprising the steps of:

(a) protecting 5'-hydroxy group of a 2'-deoxyribonucleoside;

(b) converting (S)-3'-hydroxy group of the compound obtained in step (a) into (R)-3'-hydroxy group;

(c) grafting the compound obtained in step (b) on a solid support functionalized with at least one N-hydroxyphthalimide moiety, wherein said at least one N-hydroxyphthalimide moiety is represented by formula (I):

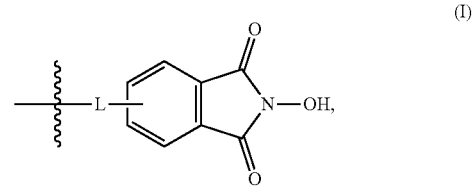

wherein L represents a linker, under conditions allowing (R)-3'-hydroxy group of the compound obtained in step (b) to be substituted by a N-hydroxyphthalimide moiety of the functionalized solid support;

(d) deprotecting 5'-hydroxy group of the compound obtained in step (c);

(e) triphosphorylating 5'-hydroxy group of the compound obtained in step (d);

(f) reacting the compound obtained in step (e) with a cleaving reagent selected from the group consisting of primary amines, hydrazine and hydroxides; and, (g) optionally recovering 3'-O-amino-2'-deoxyribonucleoside-5'-triphosphate obtained in step (f).

It also relates to a solid support functionalized with at least one N-hydroxyphthalimide moiety, wherein said at least one N-hydroxyphthalimide moiety is represented by formula (I):

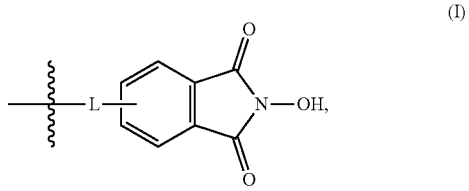

(I)

wherein L represents a linker, preferably L is —CH$_2$—NH—(CO)—.

It further relates to a 3'-O-amino-2'-deoxyribonucleoside-5'-triphosphate grafted on a solid support functionalized with at least one N-hydroxyphthalimide moiety as defined above.

A further object of the present invention is a use of a solid support functionalized with at least one N-hydroxyphthalimide moiety as defined above for protecting 3'-hydroxy group of a 2'-deoxyribonucleoside during synthesis of a nucleoside or a derivative thereof.

Another object of the present invention is a use of a 3'-O-amino-2'-deoxyribonucleoside-5'-triphosphate obtained by a method as defined above, for the synthesis of a nucleic acid strand.

A further object of the present invention is a method for preparing a nucleic acid strand comprising at least one 3'-O-amino-2'-deoxyribonucleoside-5'-triphosphate obtained by a method as defined above, comprising the steps of:

(A) coupling a 3'-O-amino-2'-deoxyribonucleoside-5'-triphosphate with a 3'-hydroxy group of a nucleotide of a nucleic acid, by means an enzyme such as a polymerase; and (B) cleaving O—N bond of 3'-O-amino-2'-deoxyribonucleoside-5'-triphosphate coupled in step (A), so as to deprotect the corresponding 3'-hydroxy group;

wherein steps A and B are cyclically carried out n times, n being an integer higher than or equal 10 to 1.

BRIEF DESCRIPTION OF THE FIGURES

FIG. 1 illustrates a method for preparing a 3'-O-amino-2'-deoxyribonucleoside-5'-triphosphate according to prior art.

DETAILED DESCRIPTION OF THE INVENTION

Definitions

According to the present invention, the terms below have the following meanings:

The terms mentioned herein with prefixes such as for example $C_1$-$C_6$, $C_1$-$C_{12}$ or $C_2$-$C_{12}$ can also be used with lower numbers of carbon atoms such as $C_1$-$C_2$, $C_1$-$C_9$, or $C_2$-$C_5$. If, for example, the term $C_1$-$C_6$ is used, it means that the corresponding hydrocarbon chain may comprise from 1 to 6 carbon atoms, especially 1, 2, 3, 4, 5 or 6 carbon atoms. If, for example, the term $C_2$-$C_5$ is used, it means that the corresponding hydrocarbon chain may comprise from 2 to 5 carbon atoms, especially 2, 3, 4, or 5 carbon atoms.

The term "alkyl" refers to a saturated, linear or branched aliphatic group. The term "($C_1$-$C_6$)alkyl" can more specifically refer to methyl, ethyl, propyl, isopropyl, butyl, isobutyl, tert-butyl, pentyl, or hexyl.

The term "alkenyl" refers to an unsaturated, linear or branched aliphatic group comprising at least one carbon-carbon double bound. The term "($C_2$-$C_6$)alkenyl" can more specifically refer to ethenyl, propenyl, isopropenyl, butenyl, isobutenyl, pentenyl, hexenyl.

The term "alkynyl" refers to an unsaturated, linear or branched aliphatic group comprising at least one carbon-carbon triple bound. The term "($C_2$-$C_{12}$)alkynyl" can more specifically refer to ethynyl, propargyl, butynyl, pentynyl, hexynyl.

The term "cycloalkyl" corresponds to a saturated or unsaturated mono-, bi- or tri-cyclic alkyl group. It also includes fused, bridged, or spiro-connected cycloalkyl groups. The term "($C_3$-$C_{12}$)cycloalkyl" can more specifically refer to cyclopropyl, cyclobutyl, cyclopentyl, and cyclohexyl. The term "cycloalkyl" may also refer to a 5-10 membered bridged carbocyclyl such as bicyclo[2,2,1]heptanyl, bicyclo[2,2,2]octanyl, or adamantyl, preferably bicyclo[2,2,1]heptanyl.

The term "aryl" corresponds to a mono- or bi-cyclic aromatic hydrocarbon. The term "($C_6$-$C_{14}$)aryl" can more specifically refer to phenyl, biphenyl, or naphthyl.

Alkyl, alkenyl, alkynyl, cycloalkyl and aryl groups as defined above also include the corresponding mono- or poly-substituted groups. Examples of substituents include, but are not limited to, ($C_1$-$C_6$)alkyl, ($C_2$-$C_6$)alkenyl, ($C_2$-$C_6$)alkynyl, ($C_3$-$C_{12}$)cycloalkyl, ($C_6$-$C_{14}$)aryl, F, Cl, Br, I, CN, NO$_2$, CF$_3$, R$^1$O—, R$^2$S—, R$^3$NH— and R$^4$R$^5$N—, R$^1$, R$^2$, R$^3$, R$^4$ and R$^5$ being each independently selected from ($C_1$-$C_6$)alkyl, ($C_2$-$C_6$)alkenyl, ($C_2$-$C_6$)alkynyl, ($C_3$-$C_{12}$)cycloalkyl and ($C_6$-$C_{14}$)aryl.

In the present invention, the terms "(S)" or "(R)" preceding a group or a moiety, such as in "(R)-3'-hydroxy group", refers to the absolute configuration of the carbon substituted by said group. The position of the carbon may also follow the terms "(S)" or "(R)". In "(R)-3'-hydroxy group", the carbon in position 3' which is substituted with a hydroxy group, has an R absolute configuration.

The term "solvent" refers to organic solvent, inorganic solvent such as water, or a mixture thereof. Examples of organic solvents include, but are not limited to, aliphatic hydrocarbons such as pentane or hexane, alicyclic hydrocarbons such as cyclohexane, aromatic hydrocarbons such as benzene, styrene, toluene, ortho-xylene, meta-xylene or para-xylene, halogenated hydrocarbons such as dichloromethane, chloroform or chlorobenzene, nitrogen-based solvents such as pyridine, acetonitrile or triethylamine, oxygen-based solvents, in particular ketones such as acetone, ethers such as diethyl ether, tert-butyl methyl ether (TBME), cyclopentyl methyl ether (CPME), tetrahydrofuran (THF) or methyl tetrahydrofuran (Me-THF), and alcohols such as methanol or ethanol, esters such as n-butyl acetate, or amides such as dimethylformamide (DMF), and mixtures thereof.

The term "acid" refers to a Brønsted or a Lewis acid. Examples of acid include, but are not limited to, hydrochloric acid, hydrobromic acid, hydriodic acid, hydrofluoric acid, nitric acid, sulfuric acid, hexafluorophosphoric acid, tetrafluoroboric acid, trifluoroacetic acid, acetic acid, sulfonic acid such as methanesulfonic acid, mono- or polycarboxylic acid, or mixtures thereof.

The term "base" refers to a Lewis or a Bronsted base. Examples of base include, but are not limited to, hydroxides such as potassium hydroxide or sodium hydroxide, carbonates such as potassium carbonate, sodium carbonate or sodium hydrogenocarbonate, alkoxides such as sodium methoxide, amines such as triethylamine, and nitrogen-based cyclic bases, such as imidazole, N-methylimidazole, pyridine or dimethyl-amino-pyridine (DMAP).

Conditions (such as temperature, concentration, equivalents of the reactants, solvents) for each step of the method of the invention are described below for particular and/or preferred embodiments, and may be adjusted by the skilled artisan using his/her general background. Each step reaction may be treated, and each intermediate or product obtained from a step reaction may be isolated, and optionally purified. Alternatively, several steps may be carried out one-pot without treating said reaction and/or isolating said reaction intermediate or reaction product. Steps of the method of the invention may be implemented in any suitable order chosen by the skilled artisan, and are preferably implemented in this given order: (a), (b), (c), (d), (e), (f), and (g). One or more of these steps may be decomposed in substeps. The "treatment" of a reaction refers to the use of reagents such as an acid or a base, and/or solvents, to stop the reaction, and typically to eliminate all or part of reaction impurities by extraction techniques and washing(s). The "purification" refers to the use of one or more techniques such as recrystallisation or chromatography, aiming at improving the purity (i.e. eliminating further reaction impurities) of the reaction product.

The method of the invention relates to the preparation of 3'-O-amino-2'-deoxyribonucleoside-5'-triphosphate starting from 2'-deoxyribonucleoside. "2'-deoxyribonucleoside" refers to a 2-deoxyribose substituted by a nitrogenous base at its anomeric carbon. In particular, said 2'-deoxyribonucleoside may be represented by the following formula (II):

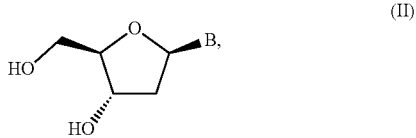

wherein B represents a nitrogenous base. Said nitrogenous base may in particular be a purine base or a pyrimidine base. Examples of purine bases include adenine and guanine. Examples of pyrimidine bases include cytosine, uracil and thymine.

The 2'-deoxyribonucleoside of adenine, guanine, cytosine, thymine and uracil, are respectively 2'-deoxyadenosine, 2'-deoxyguanosine, 2'-deoxycytidine, 2'-deoxythymidine and 2'-deoxyuridine.

In one embodiment, said nitrogenous base is in a protected form. The "protection" refers to the modification of a reactive function of a molecule by introducing a functional group, also called "protecting group", for the purpose of making said reactive function unreactive. The "deprotection" refers to the removal of said functional group, in order to free (i.e. to deprotect) said reactive function.

More particularly, a nitrogenous base having an exocyclic $NH_2$ group, such as cytosine, adenine and guanine, may be in a protected form, through protection of said $NH_2$ group. Said $NH_2$ group may be protected with an acyl group (i.e. in the form of an amide), or with an amino methylene group (i.e. in the form of an amidine). The protection of said $NH_2$ group with an acyl group may in particular be carried out by reacting the nitrogenous base with a carboxylic acid or a derivative thereof, such as an acyl chloride, an ester or an anhydride, under suitable conditions which can be easily determined by the skilled artisan. Examples of acyl group include, but are not limited to, acyl groups of formula $R^6$—C(O)—, wherein $R^6$ is selected from $(C_1-C_6)$alkyl, $(C_2-C_6)$alkenyl, $(C_2-C_6)$alkynyl, $(C_3-C_{12})$cycloalkyl and $(C_6-C_{14})$aryl. Preferred $R^6$'s are methyl, ethyl, iso-propyl, (phenoxy)methyl, (iso-propylphenoxy)methyl, (tert-butylphenoxy)methyl and phenyl.

The protection of said $NH_2$ group with an amino methylene group may in particular be carried out by reacting the nitrogenous base with an acetal, such as a N,N-Dimethylformamide dimethyl acetal, under suitable conditions which can be easily determined by the skilled artisan. Preferred amino methylene group is N,N-dimethylamino methylene group.

Preferably, cytosine is protected with an acyl group of $R^6$—C(O)—, wherein $R^6$ is methyl or phenyl.

Preferably, adenine is protected with an acyl group of $R^6$—C(O)—, wherein $R^6$ is methyl, (phenoxy)methyl or phenyl.

Preferably, guanine is protected with an acyl group of $R^6$—C(O)—, wherein $R^6$ is methyl, iso-propyl, (phenoxy)methyl, (iso-propylphenoxy)methyl or (tert-butylphenoxy)methyl, or with a N,N-dimethylamino methylene group.

In a particular embodiment, 2'-deoxyribonucleoside is selected from the group consisting of 2'-deoxythymidine, 2'-deoxyuridine, 2'-deoxycytidine, 2'-deoxyadenosine, 2'-deoxyguanosine, and a protected-base derivative thereof. "Protected-base derivative" refers to a 2'-deoxyribonucleoside whose nitrogenous base is in a protected form.

In a preferred embodiment, 2'-deoxyribonucleoside is selected from the group consisting of 2'-deoxythymidine, 2'-deoxyuridine, protected-base 2'-deoxycytidine, protected-base 2'-deoxyadenosine, and protected-base 2'-deoxyguanosine.

A process for preparing a protected-base derivative of 2'-deoxyribonucleoside can comprise the steps of:
(p1) protecting the alcohol groups of 2'-deoxyribonucleoside with a silyl group such as trimethylsilyl, preferably by reacting said 2'-deoxyribonucleoside with a suitable silylation reagent such as trimethylsilyl chloride;
(p2) protecting the $NH_2$ group of the nitrogenous base of the compound obtained in step
(p2) with an acyl group or with amino methylene group;
(p3) deprotecting the alcohols groups of the compound obtained in step (p2), preferably by reacting said compound with ammonium hydroxide.

As stated above, it is the purpose of the present invention to provide a method for preparing 3'-O-amino-2'-deoxyribonucleoside-5'-triphosphate, said method comprising the steps of:
(a) protecting 5'-hydroxy group of a 2'-deoxyribonucleoside;
(b) converting (S)-3'-hydroxy group of the compound obtained in step (a) into (R)-3'-hydroxy group;
(c) grafting the compound obtained in step (b) on a solid support functionalized with at least one N-hydroxyphthalimide moiety, wherein said at least one N-hydroxyphthalimide moiety is represented by formula (I):

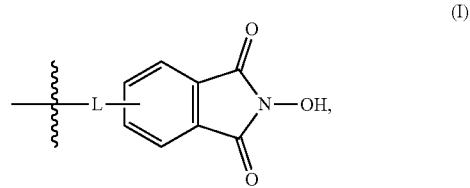

wherein L represents a linker, under conditions allowing (R)-3'-hydroxy group of the compound obtained in step (b) to be substituted by a N-hydroxyphthalimide moiety of the functionalized solid support;

(d) deprotecting 5'-hydroxy group of the compound obtained in step (c);

(e) triphosphorylating 5'-hydroxy group of the compound obtained in step (d);

(f) reacting the compound obtained in step (e) with a cleaving reagent selected from the group consisting of primary amines, hydrazine and hydroxides; and, (g) optionally recovering 3'-O-amino-2'-deoxyribonucleoside-5'-triphosphate obtained in step (f).

Step (a) of the method according to the invention consists in protecting 5'-hydroxy group of a 2'-deoxyribonucleoside.

In said step (a), 5'-hydroxy group of a 2'-deoxyribonucleoside is advantageously protected with X, X being a bulky group such as a trityl, monomethoxytrityl, dimethoxytrityl, tert-butyl dimethyl silyl, tert-butyl diphenyl silyl or triisopropylsilyl group, preferably a trityl, monomethoxytrityl or dimethoxytrityl group, and more preferably a monomethoxytrityl group. Step (a) may be carried out by reacting a 2'-deoxyribonucleoside with a reagent of formulae X-Y or (X$^+$,Y$^-$), wherein X is as defined above and Y is $BF_4$, $PF_6$, $CF_3SO_3$, $SnCl_5$, $ClO_4$ or a halogen, such as a chlorine. In a preferred embodiment, step (a) is carried out by reacting a 2'-deoxyribonucleoside with trityl chloride, monomethoxytrityl chloride or dimethoxytrityl chloride. The amount of reagent of formulae X-Y or (X$^+$,Y$^-$) may be comprised between 1 and equivalents, preferably between 1 and 2 equivalents, more preferably between 1 and 1.2 equivalents, relative to the amount of 2'-deoxyribonucleoside.

Step (a) is advantageously carried out in the presence of one or more bases. In a particular embodiment, step (a) is carried out in the presence of pyridine, and optionally triethylamine and DMAP.

In a particular embodiment, step (a) is carried out in pyridine, which acts as both a solvent and a base. The temperature in step (a) is advantageously comprised between 5° C. and 45° C., preferably between 15° C. and 30° C.

The use of a bulky protecting group advantageously makes the protection in step (a) selective, in that said 5'-hydroxy group is selectively protected over 3'-hydroxy group of the 2'-deoxyribonucleoside. The amount of 2'-deoxyribonucleoside having a 3'-hydroxy protected (with a 5'-hydroxy group protected or not) is advantageously lower than 5 mol % preferably lower than 1 mol %.

In a particular embodiment, the compound obtained in step (a), i.e. the 2'-deoxyribonucleoside having a protected 5'-hydroxy group, is directly subjected to step (b) of the method of the invention, without being isolated and/or purified. Alternatively, said compound is isolated and/or purified before to be subjected to step (b) of the method of the invention.

Step (b) of the method according to the invention aims at inverting the absolute configuration of the carbon at position 3' of the compound obtained in step (a), or in other words, converting (S)-3'-hydroxy group of said compound into (R)-3'-hydroxy group.

In one particular embodiment, step (b) of the method according to the invention is carried out under "Mitsunobu conditions". "Mitsunobu conditions" refers to conditions comprising a combination of an azo compound, a phosphorous compound and a carboxylic acid (K. C Kumara Swamy et al., "Mitsunobu and Related Reactions: Advances and Applications", Chem. Rev. 2009, 109, 2551-2651).

The term "azo compound" refers to a compound having at least one azo function, i.e. —N=N—, and more particularly to an azopyridine, an azodicarboxylic acid bis-ester or an azodicarboxylic acid bis-amide compound. Preferably, said azo compound is selected from the group consisting of di-2-methoxyethyl azodicarboxylate (DMEAD), diisopropyl azodicarboxylate (DIAD), diethyl azodicarboxylate (DEAD), 1,1'-(azodicarbonyl)dipiperidine (ADDP), di-(4-chlorobenzyl)azodicarboxylate (DCAD) and 4,4'-azopyridine, and more preferably said azo compound is DIAD.

The term "phosphorous compound" refers to a phosphine or phosphite compound. More particularly, said phosphorous compound is a compound of formula $P(R^7)_3$ wherein each of $R^7$'s, identical or different, is a $(C_1-C_6)$alkyl, a $(C_1-C_6)$alkenyl, a $(C_1-C_6)$alkynyl, a $(C_3-C_{12})$cycloalkyl or a $(C_6-C_{14})$aryl, or a compound of formula $P(OR^8)_3$ wherein each of $R^8$'s, identical or different, is a $(C_1-C_6)$alkyl, a $(C_1-C_6)$alkenyl, a $(C_1-C_6)$alkynyl, a $(C_3-C_{12})$cycloalkyl or a $(C_6-C_{14})$aryl. Preferably, said phosphorous compound is a compound of formula $P(R^7)_3$, wherein each $R^7$ represents a phenyl.

The term "carboxylic acid" refers to a compound having at least one function —C(O)OH. More particularly, said carboxylic acid may be a compound of formula $R^9C(O)OH$, wherein $R^9$ is a $(C_1-C_6)$alkyl, a $(C_1-C_6)$alkenyl, a $(C_1-C_6)$alkynyl, a $(C_3-C_{12})$cycloalkyl or a $(C_6-C_{14})$aryl, and preferably wherein $R^9$ is a phenyl.

Step (b) carried out under Mitsunobu conditions may in particular comprise the following substeps of:

(b1) reacting the compound obtained in step (a) with a carboxylic acid, in the presence of an azo compound and a phosphorous compound; and (b2) hydrolyzing the compound obtained in step (b1).

The amount of said azo compound and said phosphorous compound in step (b1), identical or different, may be comprised between 1 and 10 equivalents, preferably between 2 and 5 equivalents, relative to the amount of compound obtained in step (a). The amount of said carboxylic acid in step (b1) may be comprised between 1 and 5 equivalents, preferably between 1 and 2 equivalents, relative to the amount of compound obtained in step (a).

It is understood that "the amount of compound obtained in step (a)" as a reference for calculating equivalents refers to "the amount of compound obtained in step (a) subjected to step (b)". In the case where "the compound obtained in step (a)" is not isolated in step (a), the calculation of equivalents in step (b) is based on a total conversion of the reaction in step (a). This can also be applied for other steps or substeps.

In step (b1), the (S)-3'-hydroxy group of the compound obtained in step (a) is advantageously replaced by a (R)-3'-carboxylate group.

Hydrolyzing in step (b2) may be carried out under conditions allowing hydrolysis of said (R)-3'-carboxylate group into a (R)-3'-hydroxy group, and in particular by reacting the compound obtained in step (b1) with a hydroxide source or an alkoxide source. In a particular embodiment, said conditions also allow a deprotection of the $NH_2$ group of the nitrogenous base of the compound obtained in step (b1).

"Hydroxide source" refers to a compound which can release a hydroxide ion HO$^-$ when dissolved in a solvent. Examples of hydroxide source include, but are not limited to, potassium hydroxide, sodium hydroxide, ammonium hydroxide, tetrabutylammonium hydroxide, lithium hydroxide and cesium hydroxide.

"Alkoxide source" refers to a compound which can release an alkoxide ion ($(C_1-C_6)$alkyl-$O^-$) when dissolved in a solvent. Examples of alkoxide source include, but are not limited to, potassium methoxide and sodium methoxide.

Steps (b1) and (b2) may be carried out successively without isolating the compound obtained in step (b1). Steps (b1) and (b2) may be carried out in any organic solvent, such as THF. The temperature in steps (b1) and (b2) may independently be comprised between 5° C. and 45° C., preferably between 15° C. and 30° C.

In another particular embodiment, step (b) is carried out under phosphorous-free conditions, or in other words, in the absence of phosphorous compound.

For instance, step (b) of the method of the invention may comprise the following sub-steps:
(b1') converting (S)-3'-hydroxy group of the compound obtained in step (a) into (S)-3'-sulfonate group; and
(b2') reacting the compound obtained in step (b1') with a hydroxide source.

Preferably, said (S)-3'-sulfonate group in step (b1') is selected from the group consisting of (S)-3'-mesylate, (S)-3'-triflate and (S)-3'-tosylate group, and more preferably, said (S)-3'-sulfonate group is a (S)-3'-mesylate group.

The term "mesylate" stands for "methanesulfonate", the term "triflate" stands for "trifluoromethanesulfonate", and the term "tosylate" stands for "toluenesulfonate", in particular "para-toluenesulfonate".

Step (b1') may be carried out by reacting the compound obtained in step (a) with a suitable sulfonylation reagent, such as a sulfonyl chloride or bromide, or a sulfonic anhydride, preferably a sulfonyl chloride. Examples of sulfonyl chloride or bromide include, but are not limited to, methanesulfonyl chloride or bromide, trifluoromethanesulfonyl chloride or bromide, and para-toluenesulfonyl chloride or bromide. Examples of sulfonic anhydride include, but are not limited to, methanesulfonic anhydride, trifluoromethanesulfonic anhydride, and para-toluenesulfonic anhydride.

The amount of said sulfonylation reagent may be comprised between 1 and 5 equivalents, preferably between 1.4 and 2 equivalents, relative to the amount of compound obtained in step (a).

Step (b1') may be carried out in the presence of a base, such as triethylamine. Step (b1') may be carried out in any organic solvent, such as pyridine or dichloromethane. The temperature in step (b1') may be comprised between 5° C. and 45° C., preferably between 15° C. and 30° C.

In step (b2'), said hydroxide source may be sodium hydroxide. Said hydroxide source may be in the form of a pure solid or may be diluted in water. The amount of said hydroxide source may be comprised between 1 and 10 equivalents, preferably between 2 and 5 equivalents, relative to the amount of compound obtained in step (b1').

In a particular embodiment, the solvent in step (b2') is a mixture of an alcohol, such as ethanol, and water. The temperature in step (b2') may be comprised between 60° C. and 100° C., preferably between 70° C. and 90° C.

The $NH_2$ group of the nitrogenous base of the compound obtained in step (b1') is advantageously deprotected under conditions of step (b2'). The compound obtained in step (b2') is advantageously isolated and then purified, for instance by chromatography.

Step (c) of the method of the invention consists in grafting the compound obtained in step (b) on a solid support functionalized with at least one N-hydroxyphthalimide moiety, wherein said at least one N-hydroxyphthalimide moiety is represented by formula (I):

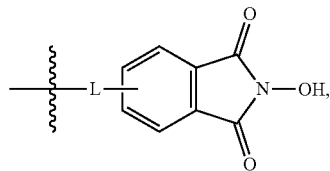

wherein L represents a linker, under conditions allowing (R)-3'-hydroxy group of the compound obtained in step (b) to be substituted by a N-hydroxyphthalimide moiety of the functionalized solid support.

Said solid support functionalized with at least one N-hydroxyphthalimide moiety can also be called "N-hydroxyphthalimide-functionalized solid support" or "functionalized solid support" in the following description.

In a particular embodiment, said N-hydroxyphthalimide-functionalized solid support is made of a material selected from the group consisting of a polystyrene resin, silica, tentagel, glass and a mixture thereof, preferably said N-hydroxyphthalimide-functionalized solid support is made of a polystyrene resin.

Said linker L refers to a chemical entity, i.e. a chemical moiety or a chemical bond, which links the N-hydroxyphthalimide group and the solid support.

In a particular embodiment, L is —$CH_2$—NH—(CO)— or is represented by the following formula (L1):

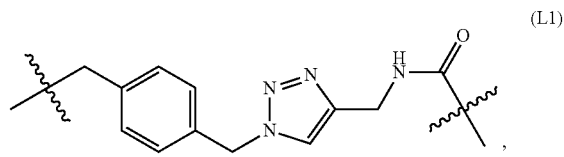 [SMILES: *Cc1ccc(Cn2cc(CNC(*)=O)nn2)cc1]

and preferably, L is —$CH_2$—NH—(CO)—.

In a preferred embodiment, said at least one N-hydroxyphthalimide moiety is represented by the following formula (Ia):

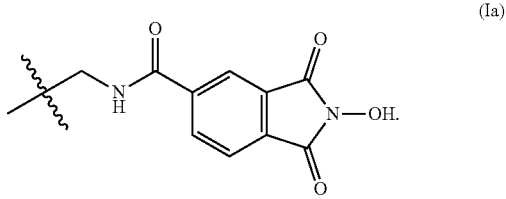 [SMILES: *CNC(=O)c1ccc2c(c1)C(=O)N(O)C2=O]

The density of N-hydroxyphthalimide moieties in said N-hydroxyphthalimide-functionalized solid support may be comprised between 0.2 and 6 mmol per gram of N-hydroxyphthalimide-functionalized solid support, preferably between 0.2 and 5, between 0.2 and 4, between 0.2 and 3, between 0.2 and 2, or between 0.2 and 1 mmol per gram of N-hydroxyphthalimide-functionalized solid support. In a particular embodiment, the density of N-hydroxyphthalimide moieties in said N-hydroxyphthalimide-functionalized solid support is comprised between 0.5 and 1, between 0.5 and 1.5, between 0.5 and 2, between 0.5 and 2.5, between 0.5 and 3, between 1 and 1.5, between 1 and 2, between 1 and 2.5, or between 1 and 3 mmol per gram of N-hydroxyphthalimide-functionalized solid support.

In one particular embodiment, step (c) comprises reacting the compound obtained in step (b) with said N-hydroxyphthalimide-functionalized solid support, in the presence of an azo compound, preferably DIAD, and a phosphorous compound, preferably a compound of formula $P(R^7)_3$, wherein each $R^7$ represents a phenyl.

The amount of said azo compound and said phosphorous compound in step (c), identical or different, may be comprised between 1 and 10 equivalents, preferably between 2 and 5 equivalents, relative to the amount of compound obtained in step (b).

In another embodiment, step (c) comprises the following substeps:
(c1) converting (R)-3'-hydroxy group of the compound obtained in step (b) into (R)-3'-sulfonate group; and
(c2) reacting the compound obtained in step (c1) with said N-hydroxyphthalimide-functionalized solid support.

Preferably, said (R)-3'-sulfonate group in step (c1) is selected from the group consisting of (R)-3'-mesylate, (R)-3'-triflate and (R)-3'-tosylate group, and more preferably, said (R)-3'-sulfonate group is a (R)-3'-mesylate group.

Conditions of step (c1) are advantageously similar to conditions of step (b1') described above.

The at least one N-hydroxyphthalimide moiety of said solid support in step (c2) is advantageously in a hydroxy-deprotonated form. Deprotonation of the hydroxy group of said at least one N-hydroxyphthalimide moiety may be carried out by contacting said N-hydroxyphthalimide-functionalized solid support with any suitable base known to the skilled artisan, such as sodium hydroxide.

Steps (c1) and (c2) may be carried out successively without isolating the compound obtained in step (c1). In particular, step (c2) may be carried out by contacting said hydroxy-deprotonated N-hydroxyphthalimide-functionalized solid support with the mixture obtained in step (c1).

The amount of N-hydroxyphthalimide moieties in step (c) may be comprised between 1 and 5 equivalents, preferably between 1.2 and 2 equivalents, relative to the amount of compound obtained in step (b). The corresponding amount of N-hydroxyphthalimide-functionalized solid support can be determined from the density of N-hydroxyphthalimide moieties in said N-hydroxyphthalimide-functionalized solid support.

The temperature in step (c) (or substeps thereof) may be comprised between 5° C. and 45° C., preferably between 15° C. and 30° C.

Conditions of step (c) allows (R)-3'-hydroxy group of the compound obtained in step (b) to be substituted by N-hydroxyphthalimide moiety of said N-hydroxyphthalimide-functionalized solid support. More specifically, the substitution advantageously occurs such that a (S)—N-hydroxyphthalimide moiety is formed. Said substitution may be described as a formal second order nucleophilic substitution.

The compound obtained in step (c) is advantageously obtained as a dispersion or suspension. Advantageously, step (c) further comprises isolating said compound, typically by filtration or centrifugation, and a washing thereof with one or more organic solvents, such as THF, dimethylsulfoxide, methanol or dichloromethane.

A step (c'), subsequent to step (c), may be carried out for capping N-hydroxyphthalimide moieties of the solid support which do not substitute the (R)-3'-hydroxy group of the compound obtained in step (b), or in other words, which did not react in step (c). Said capping step may be carried out by reacting the compound obtained in step (c) with an anhydride, such as acetic anhydride or phenoxyacetic anhydride, in the presence of at least one base, such as N-methylimidazole, pyridine or a mixture thereof, preferably a mixture thereof.

The temperature in step (c') may be comprised between 5° C. and 45° C., preferably between 15° C. and 30° C.

Step (d) consists in selectively removing the protecting group of the 5'-hydroxy group of the compound obtained in step (c) or (c'), by reacting said compound with a suitable deprotection reagent.

In one particular embodiment, said 5'-hydroxy group is protected with a group selected from trityl, monomethoxytrityl and dimethoxytrityl group, and step (d) is carried out by reacting the compound obtained in step (c) or (c') with an acid, preferably dichloroacetic acid (DCA). Said acid is advantageously diluted in a solvent such as dichloromethane.

In another particular embodiment, said 5'-hydroxy group is protected with a group selected from tert-butyl dimethyl silyl, tert-butyl diphenyl silyl and triisopropylsilyl group, and step (d) is carried out by reacting the compound obtained in step (c) or (c') with Tetra-n-butylammonium fluoride, ammonium fluoride, Triethylamine trihydrofluoride or Hydrogen fluoride pyridine.

The temperature in step (d) may be comprised between 5° C. and 45° C., preferably between 15° C. and 30° C.

The compound obtained in step (d) is advantageously obtained as a dispersion or suspension. Advantageously, step (d) further comprises isolating said compound, typically by filtration or centrifugation, and a washing thereof with one or more organic solvents, such as dichloromethane, or a mixture of dichloromethane and triethylamine.

The deprotected 5'-hydroxy group of the compound obtained in step (d) may be subjected in step (e) to a triphosphorylation, which consists in converting said 5'-hydroxy group into a 5'-triphosphate group.

Step (e) of the method according to the invention may particularly comprise the following substeps of:
(e1) reacting the compound obtained in step (d) with 2-chloro-1,3,2-benzodioxaphosphorin-4-one or phosphoryl chloride; and
(e2) reacting the compound obtained in step (e1) with a pyrophosphate salt.

Said 2-chloro-1,3,2-benzodioxaphosphorin-4-one or phosphoryl chloride may be used pure or diluted. Preferably, said 2-chloro-1,3,2-benzodioxaphosphorin-4-one or phosphoryl chloride is used diluted in one or more organic solvents such as dioxane and/or pyridine.

The amount of 2-chloro-1,3,2-benzodioxaphosphorin-4-one orphosphoryl chloride in step (e1) may be comprised between 1 and 10 equivalents, preferably between 2 and 5 equivalents, relative to the amount of compound obtained in step (d).

The compound obtained in step (e1) is advantageously obtained as a dispersion or suspension. Advantageously, step (e1) further comprises isolating said compound, typically by filtration or centrifugation, and optionally a washing thereof with one or more solvents.

Pyrophosphate salts include, but are not limited to, an alkali metal pyrophosphate such as sodium pyrophosphate, an alkali earth metal pyrophosphate such as calcium pyrophosphate, an ammonium pyrophosphate, in particular tri $(C_1$-$C_{12})$alkylammonium pyrophosphate such as tributylammonium pyrophosphate, and a mixture thereof.

In one preferred embodiment, said pyrophosphate salt is an ammonium pyrophosphate, preferably tributylammonium pyrophosphate. Said ammonium pyrophosphate may result from mixing an alkali metal pyrophosphate or an alkali earth metal pyrophosphate, with an ammonium salt, in particular ammonium bicarbonate, ammonium chloride, ammonium bromide, ammonium iodide, ammonium hexafluorophosphate, ammonium tetrafluoroborate, in particular a tri($C_1$-$C_{12}$)alkylammonium salt such as tributylammonium bicarbonate.

Said pyrophosphate salt may be used pure or diluted. Preferably, said pyrophosphate salt is used diluted in one or more organic solvents such as DMF. The amount of pyrophosphate salt in step (e2) may be comprised between 1 and 5 equivalents, preferably between 1.5 and 3 equivalents, relative to the amount of compound obtained in step (e1).

Reacting in step (e2) may be carried out in the presence of an amine, such as tributylamine.

The compound obtained in step (e2), which is advantageously obtained as a dispersion or suspension, may be isolated by filtration or centrifugation.

In a particular embodiment, step (e2) described above is followed by step (e3) which consists in reacting the compound obtained in step (e2) with a mixture comprising iodine, pyridine and water.

Steps (e1), (e2) and (e3) may be each independently carried out at a temperature comprised between 5 and 45° C., preferably between 15 and 30° C.

The compound obtained in step (e), which contains a 5'-triphosphate group, may be subjected to a step (f), which aims at forming said 3'-O-amino-2'-deoxyribonucleoside-5'-triphosphate containing a 3'-O—$NH_2$ group. Step (f) of the method according to the invention may be carried out by means of a cleaving reagent which cleaves the link between the N-hydroxyphthalimide-functionalized solid support and the nucleosidic moiety. Said cleaving reagent may be selected from the group consisting of primary amines, hydrazine and hydroxide sources.

More specifically, said cleaving reagent may be selected from the group consisting of hydrazine, lithium hydroxide, cesium hydroxide, sodium hydroxide, potassium hydroxide, ammonium hydroxide, and primary amines of formula R'—$NH_2$, wherein R' is a ($C_1$-$C_6$)alkyl, a ($C_2$-$C_6$)alkenyl a ($C_2$-$C_6$)alkynyl, a ($C_3$-$C_{12}$)cycloalkyl, or a ($C_6$-$C_{14}$)aryl. In a preferred embodiment, said cleaving reagent is a primary amine of formula R'—$NH_2$, wherein R' is a methyl.

The temperature in step (f) may be comprised between 5° C. and 45° C., preferably between 15° C. and 30° C.

Recovering 3'-O-amino-2'-deoxyribonucleoside-5'-triphosphate obtained in step (f) may be achieved by eliminating the solid support, for instance by filtration or centrifugation. Said 3'-O-amino-2'-deoxyribonucleoside-5'-triphosphate may further be purified, typically by means of a chromatography, in particular a ion-exchange chromatography. The purity of said is advantageously above 90%, preferably above 95%.

The present invention also relates to a solid support functionalized with at least one N-hydroxyphthalimide moiety, wherein said at least one N-hydroxyphthalimide moiety is represented by formula (I):

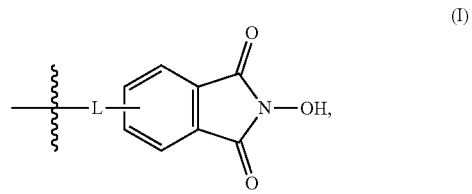

wherein L represents a linker.

In a preferred embodiment, L is —$CH_2$—NH—(CO)—.

In a particular embodiment, the N-hydroxyphthalimide-functionalized solid support is made of a material selected from the group consisting of a polystyrene resin, silica, tentagel, glass and a mixture thereof, preferably the N-hydroxyphthalimide-functionalized solid support is made of a polystyrene resin.

In a preferred embodiment, said at least one N-hydroxyphthalimide moiety is represented by the following formula (Ia):

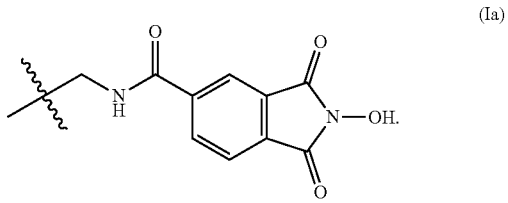 [SMILES: *CNC(=O)c1ccc2c(c1)C(=O)N(O)C2=O]

The density of N-hydroxyphthalimide moieties in said N-hydroxyphthalimide-functionalized solid support may be comprised between 0.2 and 3 mmol per gram of N-hydroxyphthalimide-functionalized solid support, preferably between 0.5 and 1.5 mmol per gram of N-hydroxyphthalimide-functionalized solid support.

A method for preparing a solid support functionalized with at least one N-hydroxyphthalimide moiety, wherein said at least one N-hydroxyphthalimide moiety is represented by formula (Ia), may comprise the following steps of:

(α) reacting a solid support functionalized with an ammonium moiety with trimellitic anhydride chloride, wherein said ammonium moiety is represented by the following formula (III),

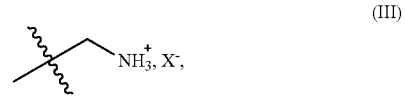

in which $X^-$ is an anion; and (β) reacting the compound obtained in step (a) with $NH_2$—OH.

Step (α) is advantageously carried out in the presence of a base. More specifically, step (α) may be decomposed in two substeps of:

(α-1) contacting said solid support functionalized with an ammonium moiety, with trimellitic anhydride chloride; and (α-2) contacting the mixture obtained in step (α-1) with a base.

A preferred base in step (α-2) is triethylamine. Steps (α-1) and (α-2) are advantageously carried out successively, in one-pot, in any organic solvent, such as dichloromethane.

Anion X⁻ may be a monoatomic or polyatomic, organic or inorganic, anion. Examples of anion include, but are not limited to, halide anions such as a chloride, a bromide or an iodide, nitrite, nitrate, sulfonate anions such as a triflate or a tosylate, hydrogenocarbonate, carboxylate anions such as acetate, formiate, trifluoroacetate or dichloroacetate, perchlorate, tetrafluoroborate, hexafluorophosphate, hexafluoroantimonate, and dihydrogenophosphate. Preferably X⁻ is a chloride.

Hydroxylamine $NH_2$—OH in step (β) is advantageously in the form of a salt of an acid, such as a hydrochloride salt. Step (β) may be carried out in the presence of a base, such as pyridine.

Step (β) may be carried out in any suitable organic solvent, at a temperature comprised between 50 and 120° C., preferably between 70 and 100° C.

The invention also relates to a 3'-O-amino-2'-deoxyribonucleoside-5'-triphosphate grafted on a solid support functionalized with at least one N-hydroxyphthalimide moiety as defined above. Said compound may in particular be the compound obtained in step (e) of the method according to the invention.

A further object of the present invention is a use of a solid support functionalized with at least one N-hydroxyphthalimide moiety as defined above for protecting 3'-hydroxy group of a 2'-deoxyribonucleoside during synthesis of a nucleoside or a derivative thereof.

Another object of the present invention is a use of a 3'-O-amino-2'-deoxyribonucleoside-5'-triphosphate obtained by a method as defined above, for the synthesis of a nucleic acid.

In the context of the invention, a "nucleic acid refers to an oligonucleotide sequence. In a particular embodiment, the nucleic acid is a DNA (DeoxyriboNucleic Acid). In another embodiment, the nucleic acid is a RNA (RiboNucleic Acid).

A further object of the present invention is a method for preparing a nucleic acid strand comprising at least one 3'-O-amino-2'-deoxyribonucleoside-5'-triphosphate obtained by a method as defined above, comprising the steps of:
  (A) coupling a 3'-O-amino-2'-deoxyribonucleoside-5'-triphosphate with a 3'-hydroxy group of a nucleotide of a nucleic acid, by means an enzyme; and
  (B) cleaving O—N bond of 3'-O-amino-2'-deoxyribonucleoside-5'-triphosphate coupled in step (A), so as to deprotect the corresponding 3'-hydroxy group; wherein steps A and B are cyclically carried out n times, n being an integer higher than or equal to 1.

In said method composed of n cycles, wherein n is as defined above, it is understood that the 3'-O-amino-2'-deoxyribonucleoside-5'-triphosphate engaged in step (A) of a cycle ("cycle k", wherein k is an integer comprised between 1 and n) may be identical to or different from the 3'-O-amino-2'-deoxyribonucleoside-5'-triphosphate engaged in step (A) of the preceding cycle ("cycle k-1").

In said method composed of n cycles, wherein n is as defined above, it is also understood that the 3'-hydroxy group deprotected in step (B) of a cycle ("cycle k", wherein k is an integer comprised between 1 and n-1) corresponds to the 3'-hydroxy group coupled with a 3'-O-amino-2'-deoxyribonucleoside-5'-triphosphate, in step (A) of the next cycle ("cycle k+1").

Said enzyme in step (A) is advantageously a polymerase.

Step (B) of cleaving O—N bond may be carried out by use of a cleaving reagent. More specifically, said 3'-O-amino-2'-deoxyribonucleoside-5'-triphosphate coupled in step (A) may be contacted with a cleaving reagent such as an oxidizing reagent or a reducing agent. The $O-NH_2$ group may be converted into a more reactive group such as a diazo compound, an O-alkylhydroxamic acid or an oxime, before or during being contacted with said cleaving reagent.

Examples of oxidizing agents include, but are not limited to, hypochlorite, nitric oxide, nitrous acid, nitrite ester, nitrosating agents, N-bromosuccinimide and N-bromoacetamide.

Examples of reducing agents include, but are not limited to, sodium amalgam, titanium (III) chloride, molybdenum hexacarbonyl, divalent vanadium, samarium, and a combination of hydrogen with a catalyst, such as a Pt or Pd catalyst.

Other type of cleaving reagents may be used, such as cupferron, acid blue 45, N-nitrosopyrrolidine, quinone, nitrobenzene or nitroolefins.

The invention will also be described in further detail in the following examples, which are not intended to limit the scope of this invention, as defined by the attached claims.

EXAMPLES

Example 1: Preparation of Solid-Supported N-Hydroxyphthalimide

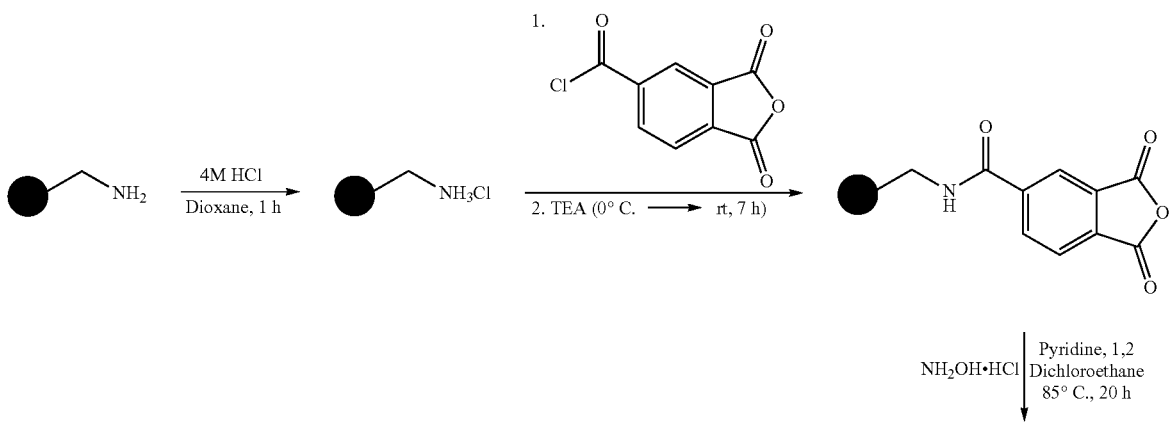

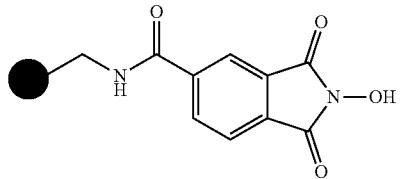

To 5.00 g Polystyrene (Loading: 1.30 mmol/g, 6.50 mmol. 1% DVB crosslinked) in a 50 mL Falcon Tube 40 mL HPLC grade dichloromethane and 8.2 mL 4 M HCl in dioxane (32.6 mmol) was added. This suspension was agitated for 1 h and afterwards filtered through a frit. The solid support was washed with $CH_2Cl_2$. The solid support was transferred to a 250 mL round bottom flask equipped with a magnetic stirring bar. 6.80 g (32.4 mmol) Trimellitic anhydride chloride was added followed by 40 mL dichloromethane and the mixture stirred. The reaction was cooled to 0° C. using an ice bath. A solution of 6.20 mL (45.4 mmol) triethylamine in 24 mL dichloromethane was added to the reaction mixture over 2 h via a syringe pump. The reaction mixture was stirred at 0° C. for an additional 3 h, warmed to rt and stirred for another 2 h. The solid support was filtered and washed with $CH_2Cl_2$, DMF, THF and $CH_2Cl_2$. Following washing, 2.25 g (32.4 mmol) hydroxylamine hydrochloride and 50 mL 3:1 pyridine/1,2-dichloroethane were added and the reaction mixture stirred for 20 h at 85° C. The reaction was cooled to rt, the resin filtered, washed with MeOH, DMF, DMF/$H_2O$ 1:1, DMF, THF, $CH_2Cl_2$ and $Et_2O$, and dried under high vacuum to give 5.80 g orange beads in 56% yield (Loading 0.73 mmol/g).

Example 2: Synthesis of 5'-O-(4-Monomethoxytrityl)-xylo-2'-deoxythymidine

Triethylamine (2.26 mL, 16.3 mmol), DMAP (0.17 g, 1.39 mmol), and then 4-monomethoxytrityl chloride (4.80 g, 15.5 mmol) were added to a stirred solution of 2'-deoxythymidine (3.28 g, 13.5 mmol) in pyridine (60 mL) at room temperature. The resulting mixture was stirred overnight at room temperature. The reaction mixture was cooled, and triethylamine (3.06 mL, 22.1 mmol) and then MsCl (1.55 mL, 20.2 mmol) were added. The mixture was stirred for 2 h at room temperature, then it was filtered, the solid was washed with ethyl acetate, and the filtrate was concentrated in vacuo. The residue was dissolved in EtOH (60 mL), and NaOH (1 M; 33 mL) was added. The mixture was heated at reflux for 1.5 h, then it was cooled to room temperature and neutralized with HCl (1% v/v; 20 mL). The ethanol was removed in vacuo, and the residue was extracted with $CH_2Cl_2$ (4×100 mL). The combined organic extracts were washed with brine, dried with $MgSO_4$, and concentrated under reduced pressure. The crude residue was purified by column chromatography on silica gel (gradient $CH_2Cl_2$/MeOH, 0 to 2.5%, v/v) to give 6.12 g 5'-O-(4-Monomethoxytrityl)-xylo-2'-deoxythymidine (11.9 mmol) as a colorless foam, in 88% yield.

Schema 2

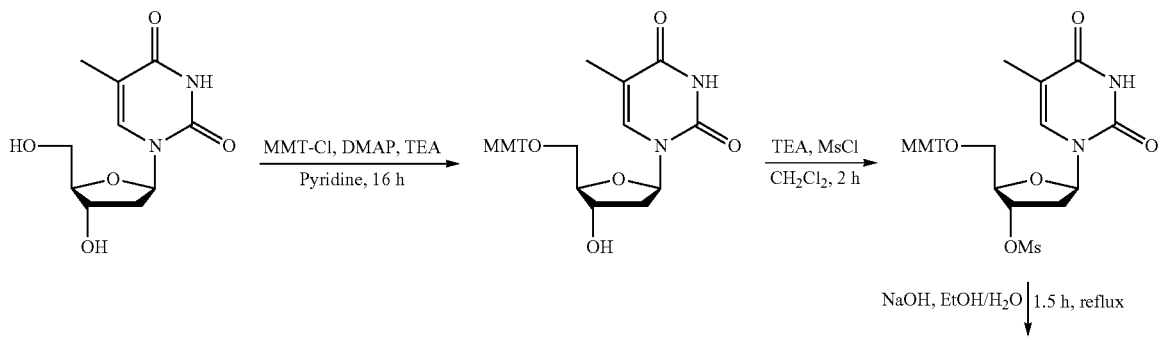

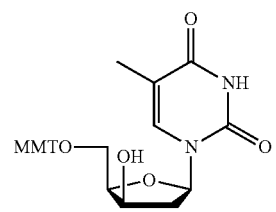

Example 3: Solid-Supported Synthesis of 3'-O-Amino-thymidine-5'-triphosphate

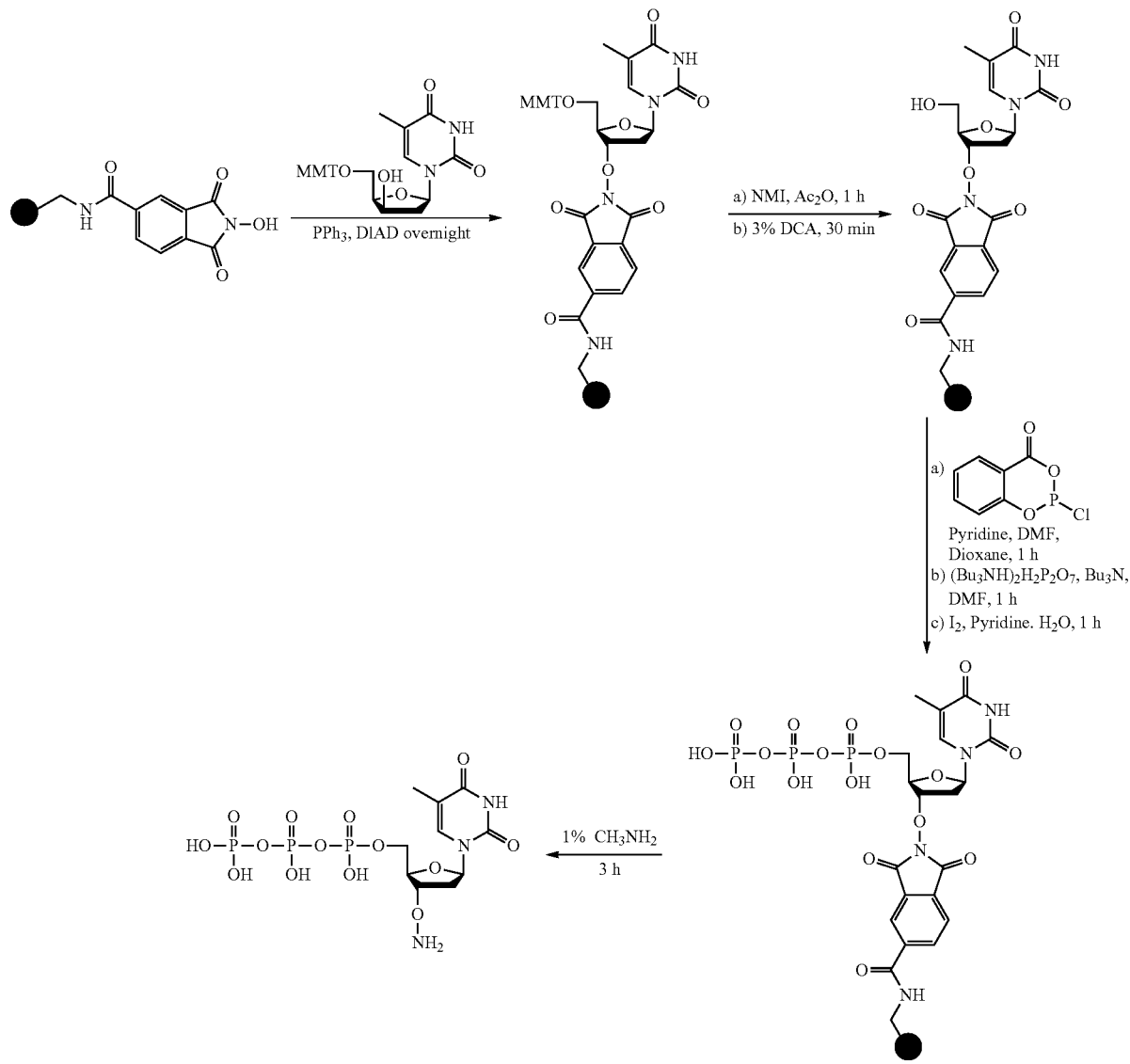

Schema 3

5'-O-(4-Monomethoxytrityl)-xylo-2'-deoxythymidine (0.465 g, 0.904 mmol) was added to 2.00 g (1.46 mmol) of the above prepared N-Hydroxyphthalimide functionalized solid-support in a 50 mL falcon tube and dissolved/suspended in 40 mL THF. Triphenylphosphine (840 mg, 3.20 mmol) was added to this solution and the falcon tube cooled in an ice bath for 5 min. Diisopropyl azodicarboxylate (0.63 mL, 3.21 mmol) was added and the falcon tube agitated for 16 h at room temperature. The solid-support was washed with THF, DMSO, THF, MeOH and $CH_2C_{12}$, followed by a 1 h capping using a mixture of 2 mL acetic anhydride, 2 mL pyridine, 34 mL THF and 2 mL N-Methylimidazole. After capping the solid-support was washed with $CH_2Cl_2$, MeOH and $CH_2Cl_2$. The detritylation was performed using 3% DCA in $CH_2Cl_2$ for 30 min. The solid-support was washed with $CH_2Cl_2$, 2% TEA containing $CH_2Cl_2$, $CH_2Cl_2$ and dried in vacuo. Freshly distilled 2-Chloro-1,3,2-benzodioxaphosphorin-4-one (640 mg, 3.16 mmol) was dissolved in 12 mL 1,4-dioxane. This solution was added to the solid support together with 3 mL pyridine. The 50 mL falcon tube containing the reaction mixture was agitated for 1 h at room temperature. The falcon tube was centrifuged to let the solid-support sediment. The upstanding solution was decanted off and discarded. Tri-n-butylammonium pyrophosphate (863 mg, 1.89 mmol) was dissolved in 7 mL DMF and added to the solid-support together with tributylamine (0.90 mL, 3.79 mmol) and agitated for 1 h at room temperature.

After centrifugation the upstanding solution was decanted off and discarded. A solution containing iodine (803 mg, 3.16 mmol), 10.5 mL THF, 3 mL pyridine and 1.5 mL water was added to the reaction mixture and agitated for 1 h at room temperature. The solid support was washed with THF, 7 mL 10% sodium thiosulfate solution, DMSO, water and MeCN. To the support 10 mL cold 1% Methylamine solution in $H_2O$/MeCN 1:1 (v/v) was added and agitated for 1 h. This solution was filtered and evaporated to dryness. Another 10 mL 1% Methylamine solution was added and incubated for 1 h (2×). At the end the support was washed with acetonitrile. The combined solutions were evaporated to obtain a yellow foam of crude 3'-O-Amino-thymidine-5'-triphosphate (270 mg).

Ion-exchange HPLC using a preparative Dionex DNAPac PA100 column showed a crude purity of 60%. Buffer A: Water, Buffer B: 1 M $NH_4HCO_3$ (pH 7.76), Gradient: 0-30% over 30 min, Flow 10 mL/min.

Ion-exchange HPLC using an analytical Dionex DNAPac PA100 column showed a purity of 90%. Buffer A: Water, Buffer B: 1 M $NH_4HCO_3$ (pH 7.76), Gradient: 0-30% over 30 min, Flow 1 mL/min, Retention time: 19.63 min. The isolated overall yield was 47 µmol (5%).

The invention claimed is:

1. A method for preparing 3'-O-amino-2'-deoxyribonucleoside-5'-triphosphate, said method comprising the steps of:
   (a) protecting 5'-hydroxy group of a 2'-deoxyribonucleoside;
   (b) converting (S)-3'-hydroxy group of the compound obtained in step (a) into (R)-3'-hydroxy group;
   (c) grafting the compound obtained in step (b) on a solid support functionalized with at least one N-hydroxyphthalimide moiety, wherein said at least one N-hydroxyphthalimide moiety is represented by formula (I):

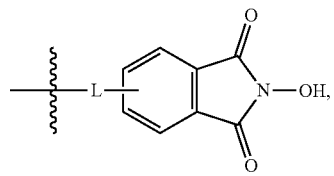

wherein L represents a linker, under conditions allowing (R)-3'-hydroxy group of the compound obtained in step (b) to be substituted by a N-hydroxyphthalimide moiety of the functionalized solid support;
   (d) deprotecting 5'-hydroxy group of the compound obtained in step (c);
   (e) triphosphorylating 5'-hydroxy group of the compound obtained in step (d);
   (f) reacting the compound obtained in step (e) with a cleaving reagent selected from the group consisting of primary amines, hydrazine and hydroxides; and,
   (g) optionally recovering 3'-O-amino-2'-deoxyribonucleoside-5'-triphosphate obtained in step (f).

2. The method according to claim 1, wherein said 2'-deoxyribonucleoside is selected from the group consisting of 2'-deoxythymidine, 2'-deoxyuridine, 2'-deoxycytidine, 2'-deoxyadenosine, 2'-deoxyguanosine, and a protected-base derivative thereof.

3. The method according to claim 1, wherein step (α) comprises reacting a 2'-deoxyribonucleoside with trityl chloride, monomethoxytrityl chloride or dimethoxytrityl chloride.

4. The method according to claim 1, wherein step (b) comprises the following sub-steps:
   (b1') converting (S)-3'-hydroxy group of the compound obtained in step (a) into (S)-3'-sulfonate group; and
   (b2') reacting the compound obtained in step (b1) with a hydroxide source.

5. The method according to claim 1, wherein step (b) is carried out in the absence of phosphorous compound.

6. The method according to claim 1, wherein step (c) is carried out in the presence of a phosphorous compound, and of an azo compound.

7. The method according to claim 1, wherein step (c) comprises the following substeps:
   (c1) converting (R)-3'-hydroxy group of the compound obtained in step (b) into (R)-3'-sulfonate group; and
   (c2) reacting the compound obtained in step (c1) with a N-hydroxyphthalimide-functionalized solid support of formula (I).

8. The method according to claim 1, wherein step (e) comprises the following sub-steps:
   (e1) reacting the compound obtained in step (d) with 2-chloro-1,3,2-benzodioxaphosphorin-4-one or phosphoryl chloride; and
   (e2) reacting the compound obtained in step (e1) with a pyrophosphate salt.

9. The method according to claim 1, wherein said cleaving reagent in step (f) is selected from the group consisting of hydrazine, lithium hydroxide, cesium hydroxide, sodium hydroxide, potassium hydroxide, ammonium hydroxide, and R'—$NH_2$, wherein R' represents a ($C_1$-$C_6$)alkyl, a ($C_2$-$C_6$)alkenyl a ($C_2$-$C_6$)alkynyl, a ($C_3$-$C_{12}$)cycloalkyl, or a ($C_6$-$C_{14}$)aryl.

10. The method according to claim 1, wherein said N-hydroxyphthalimide-functionalized solid support is made of a material selected from the group consisting of a polystyrene resin, silica, tentagel, glass, and a mixture thereof.

11. The method according to claim 1, wherein L is —$CH_2$—NH—(CO)—.

12. A 3'-O-amino-2'-deoxyribonucleoside-5'-triphosphate grafted on a solid support functionalized with at least one N-hydroxyphthalimide moiety, wherein said at least one N-hydroxyphthalimide moiety is represented by formula (I):

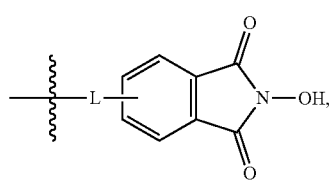

wherein L represents a linker.

13. The 3'-O-amino-2'-deoxyribonucleoside-5'-triphosphate of claim 12, wherein L is —$CH_2$—NH—C(O)—.

* * * * *